United States Patent
Lien et al.

(10) Patent No.: US 11,179,431 B2
(45) Date of Patent: Nov. 23, 2021

(54) **BIOACTIVE FRACTION OF *ANISOMELES INDICA* TSYI-813 FOR TREATING OR IMPROVING GASTRIC ULCER, ITS PREPARATION METHOD AND USE THEREOF**

(71) Applicant: Syi Biotechnology Co., Ltd., Taichung (TW)

(72) Inventors: Hsiu-Man Lien, Taichung (TW); Chia-Chang Chen, Taichung (TW); Sheau-Jiun Chang, Taichung (TW); Chao-Lu Huang, Taichung (TW)

(73) Assignee: SYI BIOTECHNOLOGY CO., LTD., Taichung (TW)

( * ) Notice: Subject to any disclaimer, the term of this patent is extended or adjusted under 35 U.S.C. 154(b) by 0 days.

(21) Appl. No.: 16/801,825

(22) Filed: Feb. 26, 2020

(65) Prior Publication Data

US 2021/0205391 A1  Jul. 8, 2021

(30) Foreign Application Priority Data

Jan. 2, 2020 (TW) .................................. 109100017

(51) Int. Cl.
*A61K 36/53* (2006.01)
*A61P 1/04* (2006.01)

(52) U.S. Cl.
CPC ................ *A61K 36/53* (2013.01); *A61P 1/04* (2018.01); *A61K 2236/333* (2013.01)

(58) Field of Classification Search
None
See application file for complete search history.

(56) References Cited

U.S. PATENT DOCUMENTS

2011/0319485 A1\* 12/2011 Lien .......................... A61P 1/04
514/468

\* cited by examiner

*Primary Examiner* — Susan Hoffman
(74) *Attorney, Agent, or Firm* — WPAT, PC

(57) ABSTRACT

Present invention provides a bioactive fraction of *Anisomeles indica*, TSYI-813, and its preparation which includes extracting *Anisomeles indica* using an alcohol solvent, fractioning the extract of *Anisomeles indica* by an organic solvent and water, and purifying via a silica column chromatography with 10:1~10:5 hexane/ethyl acetate for sequential elution to give the bioactive fraction of *Anisomeles indica*, TSYI-813. The bioactive fraction of *Anisomeles indica*, TSYI-813, disclosed in present invention can can be used as an effective ingredient for treating or improving gastric ulcers, including reducing the area of ulcer and inflammation in the stomach tissue.

6 Claims, 6 Drawing Sheets

BIOACTIVE FRACTION OF *ANISOMELES INDICA* TSYI-813 FOR TREATING OR IMPROVING GASTRIC ULCER, ITS PREPARATION METHOD AND USE THEREOF

BACKGROUND OF THE INVENTION

1. Field of the Invention

The present invention relates to the field of gastric ulcers, in particular, a bioactive fraction of *Anisomeles indica* for treating gastric ulcers.

2. Description of the Prior Art

According to statistical data, the prevalence of gastric ulcer disease (PUD) in Europe is 2%, but the rate is as high as 4.7% in Taiwan, which is 2 times higher than that in Europe. Based on the national population, nearly 1 million people in Taiwan may have gastric ulcer. Gastric ulcers tend to emerge gradually and the major pathophysiological progression of gastric ulcers can be divided into: (1) enhanced gastric acid erosion or excessive secretion of gastric juice; (2) mucosal cells cannot be repaired normally; (3) barriers between mucosal cells collapse.

Based on the abovementioned three major pathophysiological progression, the most common cause of gastric ulcer (or duodenal ulcer) is *Helicobacter pylori* infection and excessive or inappropriate use of drugs (mainly nonsteroidal anti-inflammatory drugs). Nonsteroid anti-inflammatory drugs (NSAID drugs) are commonly used anti-inflammatory and analgesic drugs, of which aspirin can inhibit blood clotting and reduce the occurrence of thrombus, therefore it is often used to prevent the recurrence of myocardial infarction or stroke. NSAID drugs are mainly used to inhibit the catalysis of cyclooxygenase (COX) to achieve the anti-inflammatory and analgesic effects and antithrombotic effects. However, taking NSAID drugs can cause reduced repair of the gastrointestinal mucosa and subsequently result in gastric ulcer.

At present, common treatments for gastric ulcers include the use of medicines such as antacids to neutralize gastric acid. However, long-term use of antacids may have the risk of extremely low level of the gastric acid and increased pH of gastric acid and may also cause overgrow of gastrointestinal bacteria. Liquid antacid is another common drug used to improve gastric ulcers and can attach to the gastric mucosa and form a protective film on the stomach wall, but it has a short duration of action and is inconvenient to use.

Therefore, how to provide an effective ingredient to improve or treat gastric ulcers without side effects is the major topic of this invention.

SUMMARY OF THE INVENTION

Present invention relates to a method for preparation of a bioactive fraction of *Anisomeles indica*, TSYI-813, and it is comprising of:
Step 1: using an alcohol solvent for extraction of *Anisomeles indica* to give an extract of *Anisomeles indica*;
Step 2: mixing the extract of *Anisomeles indica* with an organic solvent and water for fraction;
Step 3: purifying an organic layer obtained from Step 2, including the use of a silica gel column chromatography with hexane/ethyl acetate in the ratio of 10:1 to 10:5 for sequential elution, and the obtained fraction IV is the bioactive fraction of *Anisomeles indica*, TSYI-813.

According to the invention, the extraction temperature of step 1 is 50~80° C.

According to the invention, the extraction time of Step 1 is 4~8 hours.

According to the invention, the ratio of *Anisomeles indica* and the alcohol solvent used for extraction is 1 (kg): 50~70 (liter).

According to the invention, the alcohol solvent is ethanol.

In another aspect, present invention provides a fraction of *Anisomeles indica*, which is bioactive fraction of *Anisomeles indica*, TSYI-813, prepared by using the method as mentioned abovebioactive fraction.

In one aspect, present invention provides an use of the bioactive fraction of *Anisomeles indica*, TSYI-813, in the manufacture of a medicament for treating or improving gastric ulcers.

In still another aspect, present invention provides a pharmaceutical composition for treating or improving gastric ulcers, which is comprising of the bioactive fraction of *Anisomeles indica*, TSYI-813.

According to the invention, treating or improving gastric ulcers refers to reducing the affected area of gastric ulcer.

According to the invention, treating or improving gastric ulcers refers to reducing the inflammation of stomach tissue.

According to the invention, reducing the inflammation in the stomach tissue refers to reducing the production of prostaglandin E2 (PGE2).

According to the invention, reducing the inflammation in the stomach tissue refers to reducing the production of tumor necrosis factor-$\alpha$ (TNF-$\alpha$).

According to the invention, said pharmaceutical composition may further include a pharmaceutical acceptable carriers, recipients, diluents, anti-inflammatory agents, or effective ingredients for treating gastric ulcer.

Present invention also provides a food composition which is consisting of the aforementioned bioactive fraction of *Anisomeles indica*, TSYI-813.

In summary, present invention provides a bioactive fraction of *Anisomeles indica*, TSYI-813, and a preparation method thereof. The bioactive fraction of *Anisomeles indica*, TSYI-813, has the effect of treating or improving gastric ulcers and is very suitable for use as an active ingredient for treating gastric ulcers. When used as an active ingredient in the treatment of gastric ulcers, the bioactive fraction of *Anisomeles indica*, TSYI-813, provided by present invention can not only reduces the area of gastric ulcers, but also reduces the occurrence of gastric inflammation.

DETAILED DESCRIPTION OF THE PREFERRED EMBODIMENT

Figure 1:
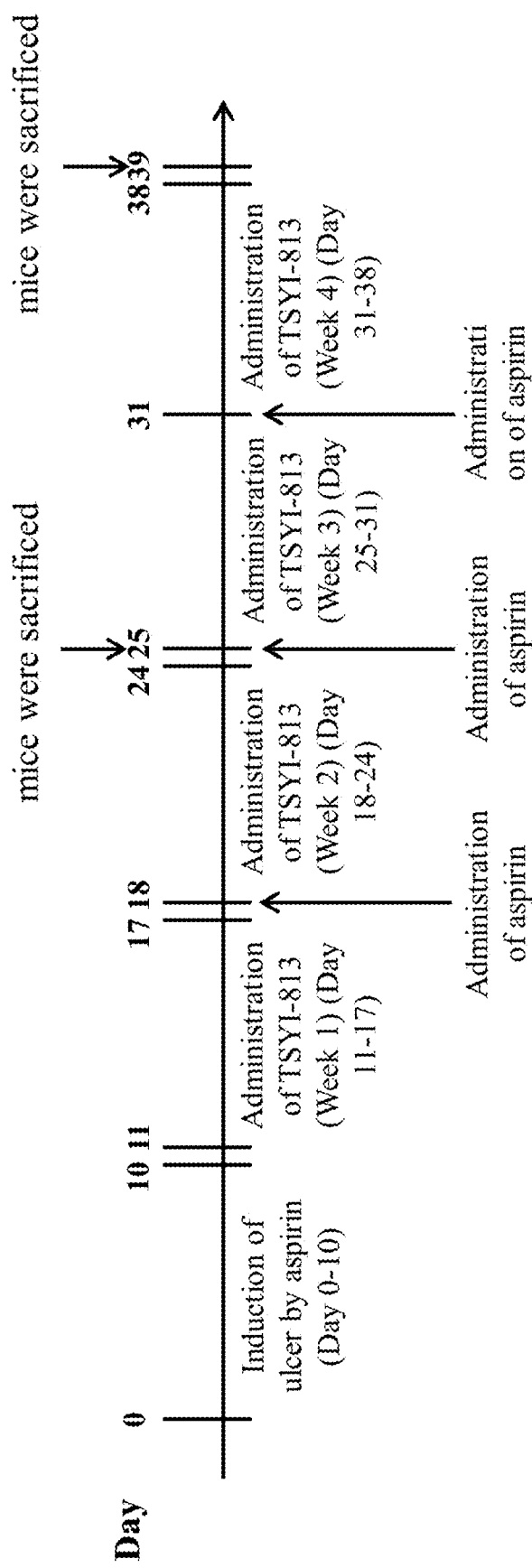
FIG. 1 is the flowchart of the gastric ulcer testtest in mice.

Unless defined otherwise, all technical and scientific terms described in this specification have the meaning commonly understood by those skilled in the art.

The singular terms "a", "an" and "the" as used in this specification and the scope of the patent application may refer to more than one subject unless otherwise stated.

"Or", "and", and "and" used in this specification refer to "or/and" unless stated otherwise. In addition, the terms "including" and "comprising" are open-ended connectives without restrictions. The preceding paragraph is a systematic reference only and should not be construed as a limitation on the subject of the invention.

The terms "treating", "for treatment" and the like refer to methods of delaying, ameliorating, reducing, or reversing a diagnosable condition suffered by a patient and the associated symptoms caused by the condition, and the methods for prevention of the condition or any related symptoms.

The term "pharmaceutically acceptable" refers to that the substance or composition must be compatible with the other ingredients of its pharmacological formulation without exacerbating the symptoms of the patient.

The composition provided by the present invention can be prepared by using technologies well known to those having ordinary knowledge in the technical field to which the present invention belongs and is prepared by combining the active ingredient or composition provided in the present invention with at least one pharmaceutically acceptable vehicle. A dosage form suitable for the composition of the present invention. The dosage forms include, but are not limited to, solutions, emulsions, suspensions, powders, lozenges, lozenges, tablets, chewing gums, capsules, and other similar or applicable dosage forms of the present invention.

The term "pharmaceutically acceptable carrier" includes one or more types of ingredients selected from the group consisting of solvents, emulsifiers, suspending agents, disintegrating agents, binding agents, excipients, stabilizers, chelating agents, diluents, gelling agents, preservatives, lubricants, surfactants, and other carriers similar or suitable for use in the present invention.

To the aforementioned composition, one or more of the abovementioned dissolution aids, buffering agents, coloring agents, flavoring agents and the like, which are generally used in the formulation field, may also be appropriately added as needed.

The term "pharmaceutically acceptable excipients" include, but are not limited to, at least one of the following: polymers, resins, plasticizers, fillers, lubricants, diluents, binders, disintegrants, solvents, co-solvents, surfactants, preservatives, sweeteners, flavoring agents, pharmaceutical-grade dyes or pigments and viscosity modifiers.

The term "pharmaceutical composition" refers to a solid or liquid composition in a form, concentration, and degree of purity suitable for administration to a patient. After administration, it can induce desired physiological changes; the pharmaceutical composition is sterile and/or non-pyrogenic.

The term "effective amount" refers to the amount necessary to produce and cause an expected response in the body, and is not a quantity required for therapeutic recovery. Those of ordinary skill in the art to which this invention pertains will understand that the effective amount of a pharmaceutical composition may vary depending on factors such as the desired biological endpoint, the bioactive agent to be delivered, the composition of the encapsulating matrix and the target tissue, etc.

The effective amount of the bioactive fraction of *Anisomeles indica*, TSYI-813, in the human body can be calculated based on the effective amount in the mice provided in the examples of this invention by using the differences in the body surface area (the conversion factor for mouse and human is 12.3-fold) and the formulas proposed by the USFDA: if the effective amount of mice is 5.2 mg/kg BW/day, then the effective amount of 40 kg human body is 5.2/12.3×40=16.9 mg/day; if the effective amount of mice is 10.4 mg/kg BW/day, the effective amount of 100 kg human body is 10.4/12.3×100=84.6 mg.

Unless otherwise specified, the materials used in the present invention are commercially available materials. *Anisomeles indica* (L.) Ktze used in the examples of the present invention can be purchased or collected in the wild. (L.) Present invention uses *Anisomeles indica* (L.) Ktze as the example, but all plants of the genus *Anisomeles* should be included in the present invention.

The test animals described in the embodiment of the present invention are 8-week-old male specific pathogen free (SPF) C57BL/6 strain mice, which were purchased from BioLASCO Taiwan Co., Ltd.

The present invention will be better elucidated when read in conjunction with the following examples; however, it should be understood that the invention is not limited to the preferred embodiments shown.

EXAMPLE 1

Preparation of the Bioactive Fraction of *Anisomeles indica*, TSYI-813

Following steps are used for preparation of the bioactive fraction of *Anisomeles indica*, TSYI-813

Step 1: using an alcohol solvent to extract *Anisomeles indica* (L.) Ktze (dried whole plant) at a certain temperature for a certain time period to give an extract of *Anisomeles indica* (L.) Ktze. The ratio of said *Anisomeles indica* (L.) Ktze and the alcohol solvent is 1 (kg):50~70 (liter) and the preferred ratio is 1 (kg):60 (liter). The alcohol solvent includes, but is not limited to, methanol, ethanol, propanol, butanol; The preferred alcohol solvent is ethanol. The volume percentage concentration of the alcohol solvent is 65-85% and the optimal concentration is 75%. The temperature condition is 50-80° C., wherein a preferred temperature condition is 70° C. The time period is 4~8 hours, wherein a preferred time period of 6 hours.

Step 2: Concentrating the extract of *Anisomeles indica* (L.) Ktze and then further extracting the concentrated extract by using an organic solvent and water to give an organic solvent layer and an aqueous layer, among which the organic solvent is comprising of, but is not limited to, phenol and chloroform, and the preferred organic solvent is chloroform.

Step 3: concentrating the organic solvent layer from Step 2, and then purifying the concentrated organic solvent layer by the Silica gel 60 Å, 230-400 mesh using 10:1~10:5 hexane/ethyl acetate for sequential elution and the fraction IV obtained after sequential elution is the bioactive fraction of *Anisomeles indica*, TSYI-813, (hereinafter called TSYI-813). Next, TSYI-813 was further concentrated and freeze-dried to give a frozen powder for following tests. One kg of the whole plant of *Anisomeles indica* can give 705 mg of the frozen powder of TSYI-813.

EXAMPLE 2

Analysis of the Effect of the Bioactive Fraction of *Anisomeles indica*, TSYI-813, on Gastric Ulcer Treatment Gastric Ulcer Test in Mice:

As shown in the flow chart of FIG. 1, the test mice were given aspirin, 500 mg per kg of weight (500 mg/kg BW), for 10 days to induce gastric ulcer. Next, the test mice were given drinking water or TSYI-813 via gavage for 4 weeks, and the dose are as follows:

Negative control group: 0.1 mL drinking water per day;

TSYI-813 low-dose group: 5.2 mg per body weight per day (5.2 mg/kg BW);

TSYI-813 middle-dose group: 10.4 mg per body weight per day (10.4 mg/kg BW).

The gastric ulcer test in mice was continued for 38 days starting from the first administration of aspirin. During the test period, the mice were weighed and a dose of the test sample (TSYI-813) corresponding to the body weight of the mice was given every day. Two weeks and four weeks after administration of TSYI-813, half of the test mice in each group were sacrificed to observe the condition of gastric ulcer in their stomach. During the test period, aspirin was given in the amount of 500 mg per kg of body weight (500 mg/kg BW) to the test mice once a week to maintain the lesion of gastric ulcer in the test mice.

Pathological Analysis of Stomach Tissue:

The image analysis software (Image J) was used to identify the ulcer lesions in the stomach tissue to calculate the ulcer area of the stomach of each test mouse, and the grade of ulcer was divided into three levels according to the area of ulcer. Next, calculate the ulcer index (UI) and curative ratios (%) according to Table 1 and the following formulas:

UI=[(1×number of level I)+(2×number of level II)+ (3×number of level III)]÷number of mice in each group Curative ratio (%)=100−(UI of test group÷UI of control group)×100

TABLE 1

| Classification and scoring of ulcer area | | | |
|---|---|---|---|
| Level | level I | level II | level III |
| Area | <1 mm2 | 1~3 mm2 | >3 mm2 |
| Score | 1 | 2 | 3 |

Figure 2A:
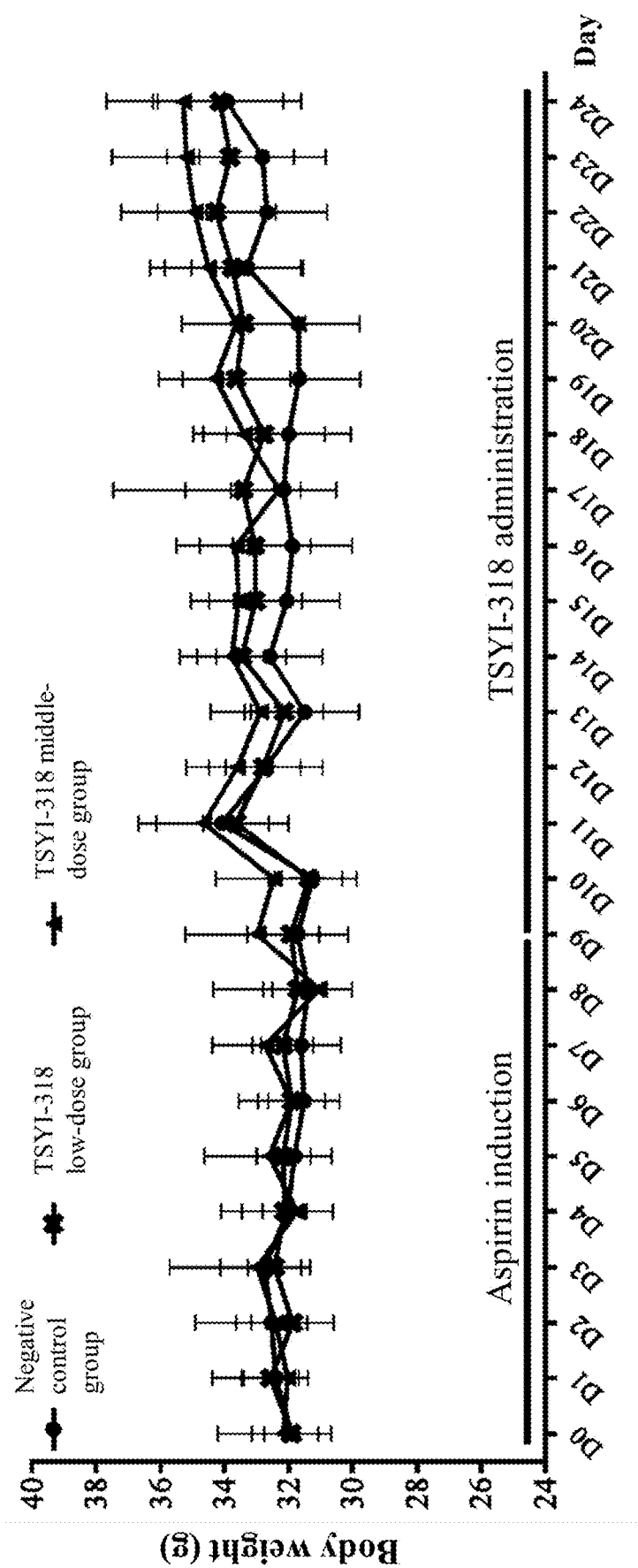
FIG. 2A shows the effect of the bioactive fraction of *Anisomeles indica*, TSYI-813, based on the changes of the body weights of mice in the gastric ulcer test; showing the changes in the weight of the test mice from Day 0 (D0) to Day 24 (D24).
Figure 2B:
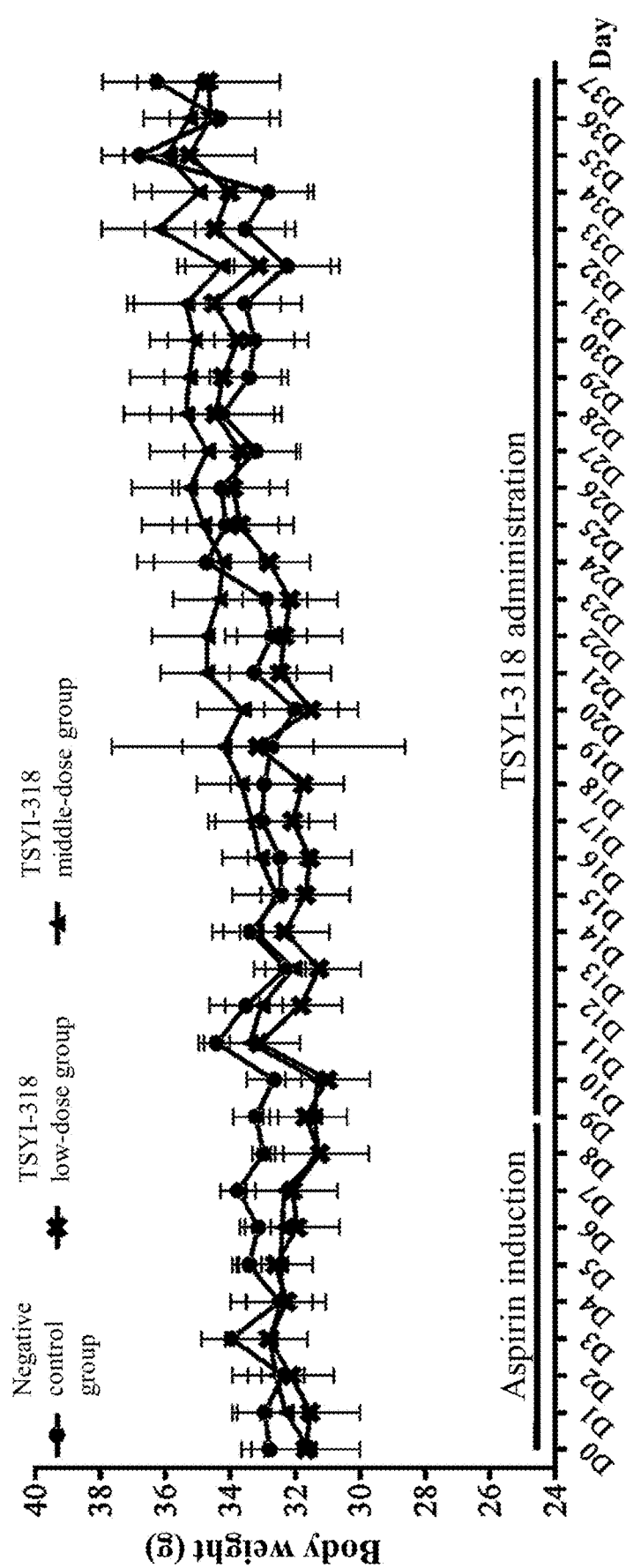
FIG. 2B shows the effect of the bioactive fraction of *Anisomeles indica*, TSYI-813, based on the changes of the body weights of mice in the gastric ulcer test; showing the changes in the weight of the test mice from Day 0 (D0) to Day 37 (D37).

Results:

The weight change of the test mice is shown in FIG. 2. The weight change between the groups is not obvious. After the mice of each group were given TSYI-813, their weight began to increase, although the average weight of the negative control group was slightly higher than TSYI-813 low-dose group and TSYI-813 middle-dose group, but there was no significant difference between that of the groups after statistical analysis.

Figure 3:
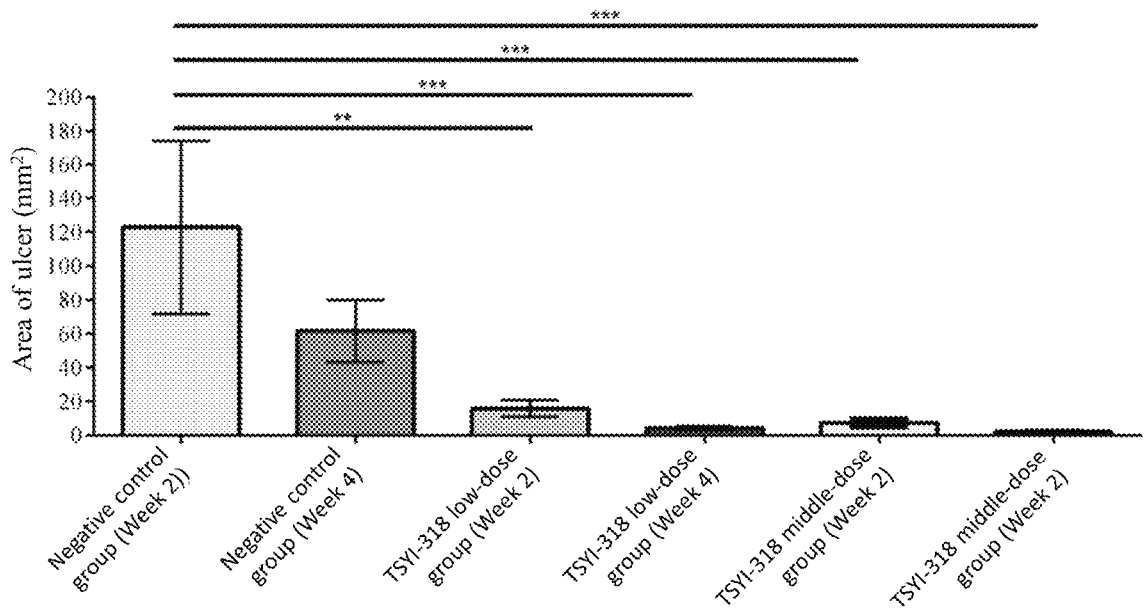
FIG. 3 shows the effect of the bioactive fraction of *Anisomeles indica*, TSYI-813, on gastric ulcer based on the changes in the affected area of gastric ulcer in the test mice.

The change in the area of gastric ulcer is shown in FIG. 3. In Week 2 and Week 4 after TSYI-813 administration, the areas of gastric ulcer in the TSYI-318 low-dose group or the TSYI-318 meddle-dose group were all smaller than that in the mice of the negative control group. This result shows that TSYI-813 has the effect of improving the area of ulcer and this effect is dose dependent.

Figure 4:
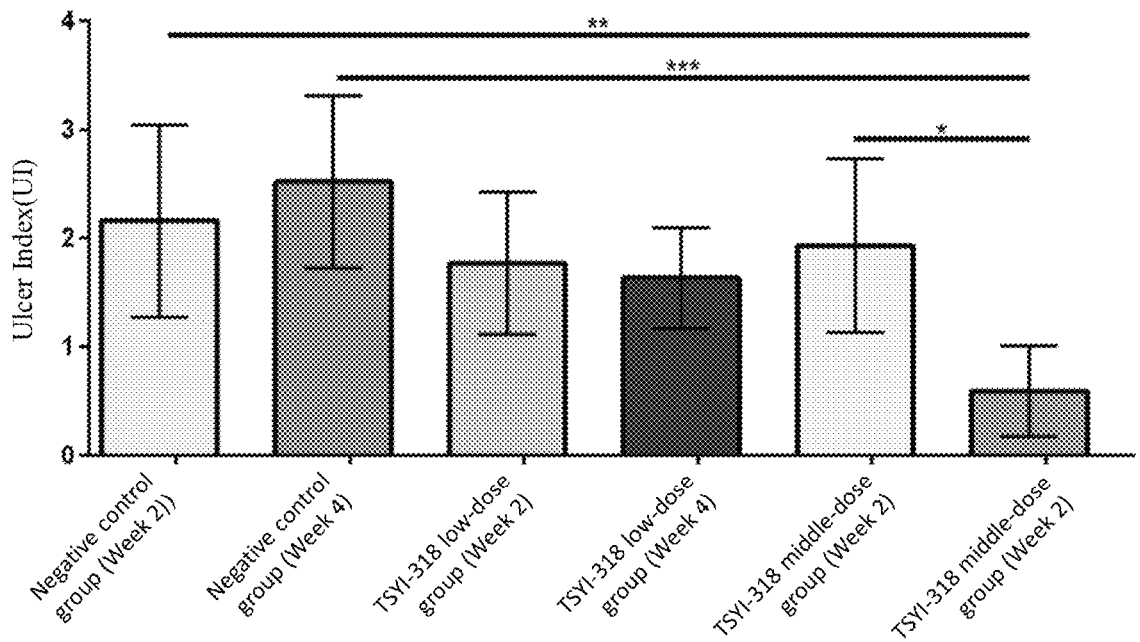
FIG. 4 shows the effect of the bioactive fraction of *Anisomeles indica*, TSYI-813, on the ulcer index in the test mice.

The calculated results of UI and curative ratio are shown in FIG. 4 and Table 2. TSYI-318 low-dose group and TSYI-318 middle-dose group, after 4 weeks of administration of TSYI-813, their UI were all lower than that of the negative control group (FIG. 4). In addition, after administration of TSYI-813 for 4 weeks, the curative ratio of the TSYI-318 low-dose group is 67.12% (Table 2). Such results indicate that TSYI-813 has the effect of treating gastric ulcer.

TABLE 2

| | Curative ratio (%) | |
|---|---|---|
| | Week 2 | Week 4 |
| TSYI-318 low-dose group | −0.84 | 9.30 |
| TSYI-318 middle-dose group | −13.45 | 67.12 |

Figures 5, 6:
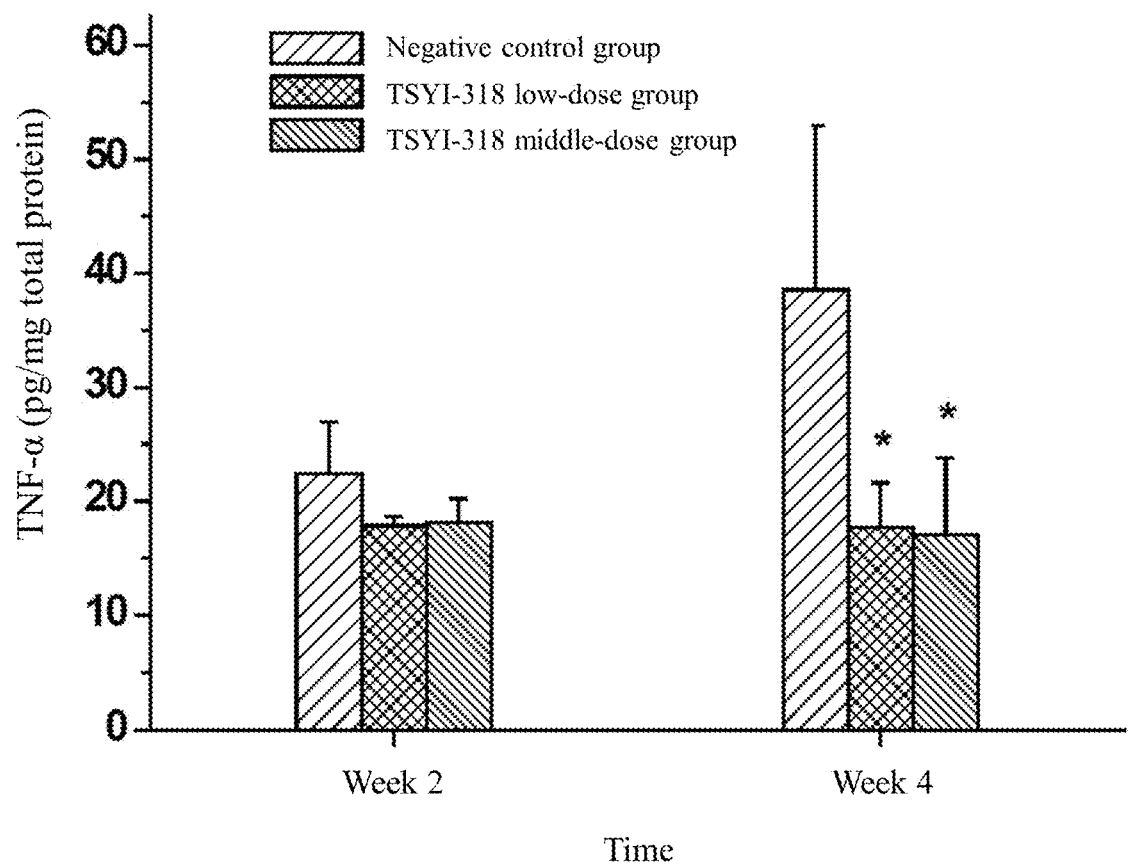
FIG. 5 shows the effect of the bioactive fraction of *Anisomeles indica*, TSYI-813, on gastric pathology in the test mice.
FIG. 6 shows the effect of the bioactive fraction of *Anisomeles indica*, TSYI-813, on the TNF-α level in the stomach tissue of the test mice.

The pathological conditions of the stomach are shown in FIG. 5. Observation of the gastric mucosal surface of the mice shows that aspirin can induce needle-like bleeding points and different sizes of ulcer lesion areas on the gastric mucosal surface of the test mice and most of the ulcer lesions appear randomly and scattered in the gastric glands. After analyzing the ulcer lesions of the test mice by image analysis software, it was found that the administration of low or meddle doses of TSYI-813 can improve the ulcer condition of the test mice (Table 3).

TABLE 3

| | Ulcer area (mm2) | |
|---|---|---|
| | Week 2 | Week 4 |
| Negative control group | 122.90 ± 51.26 | 61.55 ± 18.36 |
| TSYI-318 low-dose group | 15.80 ± 4.82 | 4.19 ± 0.66 |
| TSYI-318 middle-dose group | 7.34 ± 2.48 | 2.07 ± 0.74 |

EXAMPLE 3

Analysis of the Effect of Bioactive Fraction of *Anisomeles indica*, TSYI-813 on Biochemical Indexes of Stomach Tissue At Week 2 and Week 4 after TSYI-813 administration, the mice of each group were sacrificed and the stomach tissues were homogenized at low temperature. After centrifugation, the supernatant was analyzed for biochemical indicators related to inflammation such as prostaglandin E2 (PGE2), tumor necrosis factor-α. (TNF-α) and total protein content.

Prostaglandin E2 (PGE2) Level Analysis:

The competitive-ELISA was used to analyze the PGE2 level in stomach tissue. The test sample (the aforementioned supernatant) and a known concentration of PGE2 (PGE2 standard) were added to a 96-well microtiter plate pre-coated with mouse PGE2 antibody for reaction at 37° C. for 45 minutes, so as to allow the PGE2 or PGE2 standard in the sample competes for the PGE2 antibody binding site on the microtiter plate. Next, the excess, unbound sample or PGE2 standard was removed from the microtiter plate, and then avidin-peroxidase (avidin-HRP) was added for reaction at 37° C. for 45 minutes. Next, 3,3',5,5'-Tetramethylbenzidine (TMB) was added for 15 minutes to allow color reaction. After the reaction was stopped, the plate was analyzed by measuring the absorbance at 450 nm with a microplate reader. Finally, the absorbance of each sample was compared with the PGE2 standard curve to calculate the PGE2 concentration of each sample.

Analysis of Tumor Necrosis Factor-α (TNF-α) Level:

Sandwich-ELISA was used to analyze the TNF-α level in stomach tissues. The test sample (the aforementioned supernatant) and a known concentration of TNF-α (TNF-α standard) were added to a 96-well microtiter plate pre-coated with mouse TNF-α antibody and reacted at 37° C. for 90 minutes to allow binding of the TNF-α or TNF-α standard in the sample to the antibody. Then the mouse TNF-α antibody conjugated with avidin was added and allowed to react at 37° C. for 1 hour and the excess, unbound sample or TNF-α antibody was removed from the microtiter plate before the avidin-peroxidase (avidin-HRP) was added and incubated at 37° C. for 30 minutes; then 3,3',5,5'-tetramethylbenzidine (TMB) was added for 15 minutes to allow color reaction. After stopping the reaction, the plate was analyzed by measuring the absorbance at 450 nm with a microplate reader. Finally, the absorbance of each sample was compared with the TNF-α standard curve to calculate the TNF-α concentration of each sample.

Total Protein Content:

Bradford analysis was used to quantify the total protein content of the stomach tissue. Specifically, 1 mL of a commercially available Bradford reagent was added to a known concentration of protein standard solution (0, 25, 50, 75, and 100 ug/mL) or to 0.2 mL aforementioned supernatant (250-fold dilution), after reacting at room temperature for 2 minutes, the absorbance at 595 nm was measured and the absorbance of each sample was compared with the protein standard curve to calculate the concentration of the total protein of each sample.

The Results of Biochemical Indicators Analysis in Stomach Tissue

Figure 7:
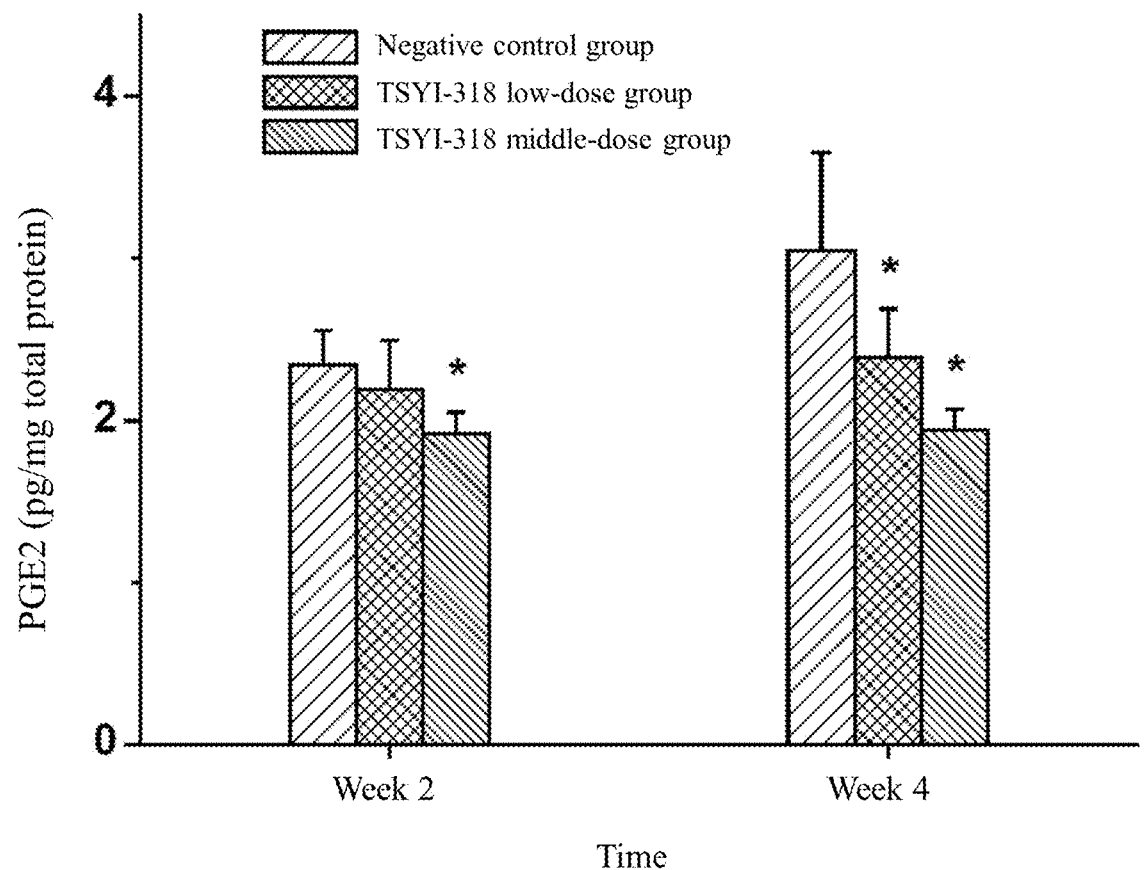
FIG. 7 shows the effect of the bioactive fraction of *Anisomeles indica*, TSYI-813, on the PGE2 level in the stomach tissue of the test mice.

The results are shown in FIG. 6, FIG. 7 and Table 4. After administration of TSYI-813 to test mice, whether at low or meddle doses, the TNF-α level in the gastric tissue of the test mice was significantly lower than that of the negative control group (FIG. 6) at Week 4. Similar results were also found in the prostaglandin 2 (PGE2). After administration of TSYI-813 at a middle dose to the test mice, PGE2 production was significantly inhibited at Week 2 and Week 4, while the production of PGE2 in the TSYI-318 low-dose group was also significantly inhibited at Week 4, and the inhibition was dose-dependent (FIG. 7). These results show that TSYI-813 can reduce the inflammation of stomach tissues, and the results indicate that TSYI-813 can inhibit inflammation in stomach tissue, thereby achieving the effect of treating gastric ulcers.

TABLE 4

| | | Inhibition (%) | |
|---|---|---|---|
| | | Week 2 | Week 4 |
| TNF-α | TSYI-318 low-dose group | 20.2 | 55.2 |
| | TSYI-318 middle-dose group | 19.2 | 56.8 |
| PGE2 | TSYI-318 low-dose group | 6.5 | 21.7 |
| | TSYI-318 middle-dose group | 18.1 | 36.3 |

According to the results mentioned above, TSYI-813 at low or middle doses has the effect of treating gastric ulcer, and the effect of 4-week TSYI-813 treatment is better than 2 weeks of TSYI-813 treatment; in addition, middle-dose TSYI-318 treatment has a better curative rate for gastric ulcer. The results of the above examples can also confirm that the bioactive fraction of *Anisomeles indica*, TSYI-813, provided by the present invention can be used as an active ingredient for treating or improving gastric ulcer and exhibits the advantages of inhibiting the production of PGE2 and TNF-α without affecting body weight.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A method for treating or improving drug-induced gastric ulcers in a subject in need comprising administering to the subject a pharmaceutical composition comprising the bioactive fraction of *Anisomeles indica*, TSYI-813, wherein the bioactive fraction of *Anisomeles indica*, TSYI-813, is prepared by a process comprising:
   Step 1: extracting *Anisomeles indica* with an alcohol solvent to give an extract of *Anisomeles indica*;
   Step 2: mixing the extract of *Anisomeles indica* with an organic solvent and water to obtain an organic solvent layer;
   Step 3: purifying the organic solvent layer including using a silica gel column chromatography with hexane/ethyl acetate in the ratio of 10:1 to 10:5 for sequential elution, and the obtained fraction IV is the bioactive fraction of *Anisomeles indica*, TSYI-813.

2. The method as recited in claim 1, wherein treating or improving gastric ulcer refers to reducing the area of gastric ulcer.

3. The method as recited in claim 1, wherein treating or improving gastric ulcer refers to reducing inflammation in the stomach tissue.

4. The method as recited in claim 3, wherein reducing inflammation in stomach tissue refers to reducing the production of prostaglandin E2 (PGE2).

5. The method as recited in claim 3, wherein reducing inflammation in stomach tissue refers to reducing the production of tumor necrosis factor-α (TNF-α).

6. The method as recited in claim 1, wherein said pharmaceutical composition further comprises pharmaceutically acceptable carriers, recipients, diluents, anti-inflammatory agents or effective ingredients for treating gastric ulcers.

* * * * *